US008852891B2

(12) United States Patent
Woo et al.

(10) Patent No.: US 8,852,891 B2
(45) Date of Patent: Oct. 7, 2014

(54) N-ACETYLGLUCOSAMINE-2-EPIMERASE AND METHOD FOR PRODUCING CMP-NEURAMINIC ACID USING THE SAME

(75) Inventors: Jin Suk Woo, Daejeon (KR); Jae Kyung Sohng, Chungcheongnam-do (KR); Byung Gee Kim, Seoul (KR); Sun Youp Kang, Daejeon (KR); Dea Hee Kim, Daejeon (KR); Kyoung Soon Jang, Seoul (KR); Ji Young Yang, Daejeon (KR); Young Soo Jung, Daejeon (KR); Won Min Seo, Daejeon (KR); Tae Geon Gil, Daejeon (KR); Sang Hee Shim, Chungcheongnam-do (KR); In Kang Hur, Daejeon (KR)

(73) Assignee: Gene Chem, Inc., Daejeon (KR)

( * ) Notice: Subject to any disclaimer, the term of this patent is extended or adjusted under 35 U.S.C. 154(b) by 1364 days.

(21) Appl. No.: 12/517,015

(22) PCT Filed: Dec. 7, 2007

(86) PCT No.: PCT/KR2007/006367
§ 371 (c)(1),
(2), (4) Date: Aug. 11, 2011

(87) PCT Pub. No.: WO2008/072861
PCT Pub. Date: Jun. 19, 2008

(65) Prior Publication Data
US 2011/0287488 A1 Nov. 24, 2011

(30) Foreign Application Priority Data

Dec. 15, 2006 (KR) ........................ 10-2006-0128422

(51) Int. Cl.
| | |
|---|---|
| C12P 19/30 | (2006.01) |
| C12N 9/90 | (2006.01) |
| C12P 19/26 | (2006.01) |
| C12P 19/34 | (2006.01) |
| C07H 21/04 | (2006.01) |
| C07K 1/00 | (2006.01) |
| C12P 17/16 | (2006.01) |

(52) U.S. Cl.
CPC .. *C12N 9/90* (2013.01); *C12P 17/16* (2013.01)
USPC .............. 435/89; 435/233; 435/84; 435/91.1; 536/23.1; 536/23.2; 530/350

(58) Field of Classification Search
USPC ........... 435/89, 233, 84, 91.1; 536/23.1, 23.2; 530/350
See application file for complete search history.

(56) References Cited

U.S. PATENT DOCUMENTS

| | | | |
|---|---|---|---|
| 6,936,173 | B2 * | 8/2005 | DeFrees ........................ 210/653 |
| 7,090,973 | B1 | 8/2006 | Breton |
| 7,863,020 | B2 * | 1/2011 | Hamilton ........................ 435/84 |
| 2002/0150968 | A1 * | 10/2002 | Wang et al. ..................... 435/53 |
| 2005/0260718 | A1 * | 11/2005 | Noguchi et al. ................ 435/97 |

FOREIGN PATENT DOCUMENTS

| | | |
|---|---|---|
| EP | 1154018 A1 | 2/2000 |
| JP | 03-180190 A | 8/1991 |
| JP | 5-211884 A | 8/1993 |
| JP | 10-004961 A | 1/1998 |
| JP | 200136982 A | 5/2001 |
| KR | 1020010102019 A | 11/2001 |
| KR | 1020060010706 A | 2/2006 |
| WO | 9526399 A1 | 10/1995 |
| WO | 2004009830 A1 | 1/2004 |

OTHER PUBLICATIONS

Cerdeno-Tarraga et al., Extensive DNA inversions in the *B.fragilis* geneome control variable gene expression. Science, 2005, vol. 307: 1463-1465.*
Frosch et al., Evidence of for a common molecular origin of the capsule gene loci in gram-negative bacteria expressing group II capsular polysaccharide. Mol. Micrbiol., 1991, vol. 5 (5): 1251-1263.*
Katinka et al., Genome sequence and gene compaction of eukaryote parasite *Encephalitozoon cuniculi*. Nature, 2001, vol. 414: 450-453.*
5 pages of Supplemental information of Katinka et al., Genome sequence and gene compaction of eukaryote parasite *Encephalitozoon cuniculi*. Nature, 2001, vol. 414: 450-453.*
Matsuyama et al., Cloning, expression, and nucleotide sequence of *Escherichia coli* K-12 ackA gene. J. Bacteriol., 1989, vol. 171 (1): 577-580.*
3 pages of Wikipedia information on Cytidylate kinase, downloaded on Jun. 7, 2013.*
XP-002614462, Full=Putative uncharacterized protein, Jun. 21, 2005, 2 pages.
European Patent Office, Supplementary European Search Report, PCT/KR2007/006367, Jan. 27, 2011.
Kornfeld, Stuart, et al., "The Feedback Control of Sugar Nucleotide Biosynthesis in Liver", PNAS, 52:371-379 (1964).
Mandel, M., et al., "Calcium-dependent bacteriophage DNA infection", Journal of Molecular Biology, 53(1):159-162 (Oct. 14, 1970).
Neumann, E., et al, "Gene transfer into mouse lyoma cells by electroporation in high electric fields", EMBO J, 1 (7):841-845 (1982).
Simon, Ethan S., et al., "Synthesis of CMP-NeuAc from N-Acetylglucosamine: Generation of CTP from CMP Using Adenylate Kinase1,2", J. Am. Chem. Soc., 110:7159-7163 (1988).

(Continued)

*Primary Examiner* — Ganapathirama Raghu
(74) *Attorney, Agent, or Firm* — Tristan A. Fuierer; Andrew D. Gerschutz; Moore & Van Allen, PLLC (57) ABSTRACT

The present invention relates to a novel N-acetylglucosamine-2-epimerase and a method for preparing CMP-N-acetylneuraminic acid, more specifically, relates to a N-acetylglucosamine-2-epimerase derived from *Bacteroides fragilis* NCTC 9343, and a method for preparing CMP-N-acetylneuraminic acid using said N-acetylglucosamine-2-epimerase. According to the present invention, CMP-N-acetylneuraminic acid can be produced economically in a large amount through a one-step reaction using cytidine monophosphate and N-acetyl-D-glucosamine which are inexpensive substrates.

6 Claims, 6 Drawing Sheets

(56) References Cited

OTHER PUBLICATIONS

Kaneko, Takakazu, et al., "Sequence Analysis of the Genome of the Unicellular Cyanobacterium *Synechocystis* sp. Strain PCC6803. II. Sequence Determination of the Entire Genome and Assignment of Potential Protein-coding Regions", DNA Research 3(3):109-136 (1996).

Tullius, Michael V., et al., "Purification, Cloning, and Expression of a Cytidine 5'-Monophosphate N-Acetylneuraminic Acid Synthetase from *Haemophilus ducreyi*", The Journal of Biological Chemistry, 271 (26):15373-15380 (1996).

Mahmoudian, M., et al., "An efficient process for production of N-acetylneuraminic acid using N-acetylneuraminic acid aldolase", Enzyme and Microbial Technology, 20:393-400 (1997).

Nakamura, Y., et al., "CyanoBase, a www database containing the complete nucleotide sequence of the genome of *Synechocystis* sp. strain PCC6803", Nucleic Acids Research, 26(1):63-67 (1998).

Tholudur, Arun, et al., "Mathematical modeling and optimization of cellulase protein production using *Trichoderma reesei* RL-P37", Biotechnology and Bioengineering, 66(1):1-16 (Mar. 26, 1999).

Littlechild, JA, et al., "A new method for the purification of 30S ribosomal proteins from *Escherichia coli* using nondenaturing conditions", Biochemistry, 17(16):3363-3369 (1978) (abstract).

Van Rinsum, Johanna, et al., "Subcelluar localization and tissue distribution of sialic acid precursor-forming enzymes", Biochem. J., 210:21-28 (1983).

Kim, Mahn Joo, et al., "Enzymes in carbohydrate synthesis: N-acetylneuraminic acid aldolase catalyzed reactions and preparation of N-acetyl-2-deoxy-D-neuraminic acid derivatives", J. Am. Chem. Soc., 110(19):6481-6486 (1988).

\* cited by examiner

SEQUENCE LISTING

```
<160> NUMBER OF SEQ ID NOS: 16

<210> SEQ ID NO 1
<211> LENGTH: 1185
<212> TYPE: DNA
<213> ORGANISM: Bacteroides fragilis

<400> SEQUENCE: 1
atgaatacta cagaatattt acagacttgg tctgactctt ataaaaatga catgataagc      60
aacatcatgc ccttttggat gaaatatggt tgggatcgca agaacggagg tgtttatacc     120
tgcgtcgacc gtgatggtca gttgatggat accaccaaat ctgtttggtt ccaagggaga     180
tttgctttta catgttcata tgcatataat cacattgagc gtaatactga atggttggca     240
gctgcgaaaa gcactctcga tttcatagaa gcacattgtt ttgatacgga tggacgtatg     300 tttttttgaag taaccgagac cggattacct attcgtaaac gtcgttatgt cttttctgaa     360
acatttgctg ctattgcaat gtccgaatat gccattgcat caggagatca tagttatgct     420
gtaaaagctt tgaaattgtt caatgatatc cgtcacttcc tttcgactcc gggaatcctg     480
gagcccaaat attgtgaacg tgtacagatg aagggacatt ctattattat gattcttatc     540
aatgtagctt cccgcattcg cgccgctatt aacgatccgg ttttggatcg gcaaatagag     600
gagtctatag caattctgca caaagacttt atgcatccgg agtttaaagc tctgcttgag     660
actgtaggtc ccaatggaga gtttatagat acgaacgcca ctcgtaccat taatcccggt     720
cattgtatcg agacctcatg gtttattttg gaagaagcca agaaccgcaa ttgggataag     780
gaaatggttg atacagcact tacgattctg gattggtcgt gggagtgggg ctgggacaaa     840
gaatacgggg gtattataaa tttccgtgat tgtcgaaacc tgccttcaca ggattatgcc     900
catgacatga agttctggtg gccacagacc gaagcgatta tcgcaactct atatgcgtat     960
caagctacta aaaatgaaaa atatctggct atgcataaac agatcagtga ctggacttat    1020
gcccattttc ctgatgcaga gtttggtgaa tggtatgggt atctccatcg tgacggaacg    1080
atttctcagc ctgcgaaagg aaatctgttt aagggaccat tccacattcc tagaatgatg    1140
```
acgaaaggct acgcactttg tcaggaatta ctgtcagaaa aataa                              1185

<210> SEQ ID NO 2
<211> LENGTH: 394
<212> TYPE: PRT
<213> ORGANISM: Bacteroides fragilis

<400> SEQUENCE: 2

Met Asn Thr Thr Glu Tyr Leu Gln Thr Trp Ser Asp Ser Tyr Lys Asn
1               5                   10                  15

Asp Met Ile Ser Asn Ile Met Pro Phe Trp Met Lys Tyr Gly Trp Asp
            20                  25                  30

Arg Lys Asn Gly Gly Val Tyr Thr Cys Val Asp Arg Asp Gly Gln Leu
        35                  40                  45

Met Asp Thr Thr Lys Ser Val Trp Phe Gln Gly Arg Phe Ala Phe Thr
    50                  55                  60

Cys Ser Tyr Ala Tyr Asn His Ile Glu Arg Asn Thr Glu Trp Leu Ala
65                  70                  75                  80

Ala Ala Lys Ser Thr Leu Asp Phe Ile Glu Ala His Cys Phe Asp Thr
                85                  90                  95

Asp Gly Arg Met Phe Phe Glu Val Thr Glu Thr Gly Leu Pro Ile Arg
            100                 105                 110

Lys Arg Arg Tyr Val Phe Ser Glu Thr Phe Ala Ala Ile Ala Met Ser
        115                 120                 125

Glu Tyr Ala Ile Ala Ser Gly Asp His Ser Tyr Ala Val Lys Ala Leu
    130                 135                 140

Lys Leu Phe Asn Asp Ile Arg His Phe Leu Ser Thr Pro Gly Ile Leu
145                 150                 155                 160

Glu Pro Lys Tyr Cys Glu Arg Val Gln Met Lys Gly His Ser Ile Ile
                165                 170                 175

Met Ile Leu Ile Asn Val Ala Ser Arg Ile Arg Ala Ala Ile Asn Asp
            180                 185                 190

Pro Val Leu Asp Arg Gln Ile Glu Glu Ser Ile Ala Ile Leu His Lys
        195                 200                 205

Asp Phe Met His Pro Glu Phe Lys Ala Leu Leu Glu Thr Val Gly Pro
    210                 215                 220

Asn Gly Glu Phe Ile Asp Thr Asn Ala Thr Arg Thr Ile Asn Pro Gly
225                 230                 235                 240

His Cys Ile Glu Thr Ser Trp Phe Ile Leu Glu Glu Ala Lys Asn Arg
                245                 250                 255

Asn Trp Asp Lys Glu Met Val Asp Thr Ala Leu Thr Ile Leu Asp Trp
            260                 265                 270

Ser Trp Glu Trp Gly Trp Asp Lys Glu Tyr Gly Gly Ile Ile Asn Phe
        275                 280                 285

Arg Asp Cys Arg Asn Leu Pro Ser Gln Asp Tyr Ala His Asp Met Lys
    290                 295                 300

Phe Trp Trp Pro Gln Thr Glu Ala Ile Ile Ala Thr Leu Tyr Ala Tyr
305                 310                 315                 320

Gln Ala Thr Lys Asn Glu Lys Tyr Leu Ala Met His Lys Gln Ile Ser
                325                 330                 335

Asp Trp Thr Tyr Ala His Phe Pro Asp Ala Glu Phe Gly Glu Trp Tyr
            340                 345                 350

Gly Tyr Leu His Arg Asp Gly Thr Ile Ser Gln Pro Ala Lys Gly Asn
        355                 360                 365

Leu Phe Lys Gly Pro Phe His Ile Pro Arg Met Met Thr Lys Gly Tyr
    370                 375                 380

Ala Leu Cys Gln Glu Leu Leu Ser Glu Lys
385                 390

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
ctgccatggt tatgaatact acag                                              24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
aatggatcct tattttctg acag                                               24

<210> SEQ ID NO 5
<211> LENGTH: 893
<212> TYPE: DNA
<213> ORGANISM: Escherichia coli

<400> SEQUENCE: 5
atggcaacga atttacgtgg cgtaatggct gcactcctga ctccttttga ccaacaacaa        60
gcactggata aagcgagtct gcgtcgcctg gttcagttca atattcagca gggcatcgac       120
ggtttatacg tgggtggttc gaccggcgag gcctttgtac aaagcctttc cgagcgtgaa       180
caggtactgg aaatcgtcgc cgaagagggc aaaggtaaga ttaaactcat cgcccacgtc       240
ggttgcgtca cgaccgccga aagccaacaa cttgcggcat cggctaaacg ttatggcttc       300
gatgccgtct ccgccgtcac gccgttctac tatcctttca gctttgaaga acactgcgat       360
cactatcggg caattattga ttcggcggat ggtttgccga tggtggtgta caacattcca       420
gccctgagtg gggtaaaact gaccctggat cagatcaaca cacttgttac attgcctggc       480
gtaggtgcgc tgaaacagac ctctggcgat ctctatcaga tggagcagat ccgtcgtgaa       540
catcctgatc ttgtgctcta taacggttac ggagaaatct tcgcctctgg tctgctggcg       600
ggcgctgatg gtggtatcgg cagtacctac aacatcatgg gctggcgcta tcagggggatc     660 gttaaggcgc tgaaagaagg cgatatccag accgcgcaga aactgcaaac tgaatgcaat       720
aaagtcattg atttactgat caaaacgggc gtattccgcg gcctgaaaac tgtcctccat       780
tatatggatg tcgtttctgt gccgctgtgc cgcaaaccgt ttggaccggt agatgaaaaa       840
tatcagccag aactgaaggc gctggcccag cagttgatgc mgagcgcggg tga             893

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6

-continued

| | |
|---|---|
| ggtatccatg gcaacgaatt tacg | 24 |

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7

| | |
|---|---|
| ggtaggctcg agcgagggga aac | 23 |

<210> SEQ ID NO 8
<211> LENGTH: 663
<212> TYPE: DNA
<213> ORGANISM: Escherichia coli

<400> SEQUENCE: 8

| | |
|---|---|
| atgaagacat acaagattgc cgttgatggg cctgctgcga gcggaaaaag cagcacatcc | 60 |
| gacttggttg caaggaaact ggggttttcc catctgatat ctggaaatct gtatagagct | 120 |
| gtgacatatg gtctggtaag gcgctttgga gaggtgcgtc caggagacga ggaacagaaa | 180 |
| agatttgttc ttgagctgag tatagaggta aggaacaaca gggtattcct agacggagag | 240 |
| gacgtgtcgg agagcctccg taaggaggtg gtcgaccgcc acgttgtttc tgttgcaagg | 300 |
| gagaaatata tccgggaaaa agtgtttaca attcagaggt cggtgataga ccttgagaag | 360 |
| aggggaatag ttgtggatgg aagagatata gccaccagga taatgccaaa tgcagatctg | 420 |
| aaggtgtttc ttacagcaag cccggagacg agggccagaa gaagatacat ggaaggcggg | 480 |
| tctgagtcct acgaggaact gctcgagtcc ataaaaaaaa gagatcacaa cgatagaaca | 540 |
| agggagcatg atccccttgt tgccacctgc gattctattg ttatcgaaaa tgacagcatg | 600 |
| acattggagg aaacagccga cgaaatcata aggctcttca gaagagtaga gtctttaat | 660 |
| taa | 663 |

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9

| | |
|---|---|
| catatgacgg caattgcccc ggttattac | 29 |

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10

| | |
|---|---|
| gaattcggtc gcttatgcga gagcc | 25 |

<210> SEQ ID NO 11
<211> LENGTH: 1203
<212> TYPE: DNA
<213> ORGANISM: Escherichia coli

<400> SEQUENCE: 11

| | |
|---|---|
| atgtcgagta agttagtact ggttctgaac tgcggtagtt cttcactgaa atttgccatc | 60 |

```
atcgatgcag taaatggtga agagtacctt tctggtttag ccgaatgttt ccacctgccc      120
gaagcacgta tcaaatggaa aatggacggc aataaacagg aagcggcttt aggtgcaggc      180
gccgctcaca gcgaagcgct caactttatc gttaatacta ttctggcaca aaaaccagaa      240
ctgtctgcgc agctgactgc tatcggtcac cgtatcgtac acggcggcga aaagtatacc      300
agctccgtag tgatcgatga gtctgttatt cagggtatca agatgcagc ttcttttgca       360 ccgctgcaca acccggctca cctgatcggt atcgaagaag ctctgaaatc tttcccacag      420
ctgaaagaca aaaacgttgc tgtatttgac accgcgttcc accagactat gccggaagag      480
tcttacctct acgccctgcc ttacaacctg tacaaagagc acggcatccg tcgttacggc      540
gcgcacggca ccagccactt ctatgtaacc caggaagcgg caaaaatgct gaacaaaccg      600
gtagaagaac tgaacatcat cacctgccac ctgggcaacg tggttccgt ttctgctatc       660 cgcaacggta aatgcgttga cacctctatg ggcctgaccc cgctggaagg tctggtcatg      720
ggtacccgtt ctggtgatat cgatccgcg atcatcttcc acctgcacga caccctgggc       780
atgagcgttg acgcaatcaa caaactgctg accaaagagt ctggcctgct gggtctgacc      840
gaagtgacca cgcgactgccg ctatgttgaa gacaactacg cgacgaaaga agacgcgaag      900
cgcgcaatgg acgtttactg ccaccgcctg gcgaaataca tcggtgccta cactgcgctg      960
atggatggtc gtctggacgc tgttgtattc actggtggta tcggtgaaaa tgccgcaatg     1020
gttcgtgaac tgtctctggg caaactgggc gtgctgggct ttgaagttga tcatgaacgc     1080
aacctggctg cacgttttcgg caaatctggt ttcatcaaca aagaaggtac ccgtcctgcg     1140
gtggttatcc caaccaacga agaactggtt atcgcgcaag acgcgagccg cctgactgcc     1200
tga                                                                   1203
```

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
catatgtcga gtaagttagt ttctg                                            25

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
gaatcctcag gcagtcaggc ggctcgcgtc                                       30

<210> SEQ ID NO 14
<211> LENGTH: 687
<212> TYPE: DNA
<213> ORGANISM: Neisseria meningitidis

<400> SEQUENCE: 14
atggaaaaac aaaatattgc ggttatactt gcgcgccaaa actccaaagg attgccatta      60
aaaaatctcc ggaaaatgaa tggcatatca ttacttggtc atacaattaa tgctgctata      120
tcatcaaagt gttttgaccg cataattgtt tcgactgatg gcgggttaat tgcagaagaa      180

```
gctaaaaatt tcggtgtcga agtcgtccta cgccctgcag agctggcctc cgatacagcc      240
agctctattt caggtgtaat acatgcttta gaaacaattg gcagtaattc cggcacagta      300
accctattac aaccaaccag tccattacgc acagggctc atattcgtga agcttttct        360 ctatttgatg agaaaataaa aggatccgtt gtctctgcat gcccaatgga gcatcatcca      420
ctaaaaaccc tgcttcaaat caataatggc gaatatgccc ccatgcgcca tctaagcgat      480
ttggagcagc ctcgccaaca attacctcaa gcatttaggc ctaatggtgc aatttacatt      540
aatgatactg cttcactaat tgcaaataat tgtttttta tcgccccaac caaactttat       600
attatgtctc atcaagactc tatcgatatt gatactgagc ttgatttaca acaggcagaa      660
aacattctta atcacaagga aagctaa                                          687

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
aagcatatgg aaaaacaaaa tattgcg                                           27

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
gtggaattct tagctttcct tgtg                                              24
```

N-ACETYLGLUCOSAMINE-2-EPIMERASE AND METHOD FOR PRODUCING CMP-NEURAMINIC ACID USING THE SAME

CROSS-REFERENCE TO RELATED APPLICATIONS

This application is filed under the provisions of 35 U.S.C. §371 and claims the priority of International Patent Application Ser. No. PCT/KR2007/006367 filed on Dec. 7, 2007 entitled "Novel N-Acetylglucosamine-2-Epimerase and Method for Producing CMP-Neuraminic Acid Using the Same" in the name of Jin Suk WOO, et al., which claims priority of Korean Patent Application No. 10-2006-0128422 filed on 15 Dec. 2006, both of which are hereby incorporated by reference herein in their entirety.

TECHNICAL FIELD

The present invention relates to a novel N-acetylglucosamine-2-epimerase and a method for producing CMP-N-acetylneuraminic acid, and more particularly, to an N-acetylglucosamine-2-epimerase derived from *Bacteroides fragilis* NCTC 9343, and a method for producing CMP-N-acetylneuraminic acid using said N-acetylglucosamine-2-epimerase.

BACKGROUND ART

Recently, as studies on the structures and functions of sugar chains are rapidly progressing, the development of the use of physiologically active oligosaccharides, glycolipids and glycoproteins and the like as drugs or functional materials has received attention. Among them, sialic acid-containing sugar chains having N-acetylneuraminic acid (NeuAc) at the terminal end have important functions, such as functioning as receptors upon cell adhesion or virus infection.

The sialic acid-containing sugar chains are generally synthesized through the catalysis of sialic acid transferase. Sialic acid transferase is an enzyme that uses CMP-N-acetylneuraminic acid (CMP-NeuAc) as a sugar donor to transfer sialic acid to receptors such as sugar chains. However, CMP-NeuAc that is used as a sugar donor is very expensive and is supplied only in a small amount only enough to be used for a reagent.

Known methods for producing CMP-NeuAc include a method for synthesizing CMP-NeuAc by the action of CMP-NeuAc synthetase using 5'-cytidine triphosphate (CTP) and N-acetylneuraminic acid (NeuAc) as substrates, but CTP and NeuAc that are used as raw materials for producing CMP-NeuAc are expensive, and thus CMP-NeuAc synthesized using these materials is also expensive.

Recently, a method for combining *Brevibacterium ammoniagenes*, which converts orotic acid to uridine 5'-triphosphate (UTP), with a recombinant *E. coli*, which produces CTP synthetase catalyzing a reaction for converting UTP to CTP, and a recombinant *E. coli*, which produces CMP-NeuAc synthetase, and synthesizing CMP-NeuAc in the recombinant organisms using orotic acid and NeuAc as raw materials, was developed. Although this method does not use expensive CTP, it is not considered to be a practical method, because the process is complicated, for example, due to the preparation of a recombinant strain using a plurality of kinds of bacterial strains, a large-sized system for carrying out the process should be prepared, and expensive NeuAc is used as a raw material.

Meanwhile, with respect to the preparation of NeuAc, a method comprising collecting colominic acid, which is a sialic acid polymer, from microorganisms, and chemically decomposing the collected colominic acid, is known, but a method for producing NeuAc using an enzyme was recently developed.

Reported methods for producing CMP-neuraminic acid (CMP-NeuAc) include: (1) a method for producing CMP-NeuAc from N-acetyl-D-mannosamine (ManNAc) using N-acetylneuraminic acid lyase or N-acetylneuraminic acid synthetase (*J. Am. Chem. Soc.*, 110:6481, 1988; *J. Am. Chem. Soc.*, 110:7159, 1988; Japanese Patent Publication 10-4961); (2) a method for producing CMP-NeuAc by converting N-acetylglucosamine (GlcNAc) to N-acetylmanosamine (ManNAc) in an alkaline condition and adding N-acetylneuraminic acid lyase or N-acetylneuraminic acid synthetase thereto to produce N-acetylneuraminic acid (NeuAc) (Japanese Patent Pubblication 5-211884; *Biotechnol. Bioeng.*, 66:2, 1999; *Enzyme Microb. Technol.*, 20, 1997), (3) a method for producing CMP-NeuAc from GlcNAc using N-acetylglucosamine (GlcNAc) 2-epimerase catalyzing the conversion of GlcNAc to MamNAc, and NeuAc lyase or synthetase (WO 95/26399; Japanese Patent Publication 3-180190; Japanese Patent Publication 2001-136982); and (4) a method for synthesizing CMP-N-acetylneuraminic acid using *E. coli* and yeast strains (WO 2004/009830).

However, the method (1) has a problem in that the raw material N-acetylmanosamine (ManNAc) is expensive, and the method (2) uses inexpensive N-acetylglucosamine (GlcNAc), but has a problem in that the process of purifying ManNAc in the mixture of GlcNAc and N-acetylmanosamine (ManNAc) is complicated. Also, the method (3) has a problem in that, because GlcNAc2-epimerase requires expensive ATP, ATP must be added or must be produced from ATP precursor adenine using microorganisms, and the method (4) has a problem in that the process is complicated due to the use of *E. coli* and yeast cells.

N-acetylglucosamine-2-epimerase is known to be found in the kidneys, liver, spleen, brain, intestinal mucosa, thymus, pancreas and salivary gland of pigs or rats, the characteristics thereof have been examined with respect to pig-derived enzymes, and the epimerase enzyme has been extracted mainly from animal-derived genes and studied (*Biochemistry*, 17:3363, 1970; *Biochem. J.*, 210:21, 1983; *PNAS*, 52:371, 1964). Also, as the N-acetylglucosamine-2-epimerase gene, a pig-derived gene is known (*J. Biol. Chem.*, 271: 16294, 1996). Among microorganisms, the entire genome sequence of *Synechocystis* sp. PCC 6803), a kind of *Cyanobacteria*, was determined, and N-acetylglucosamine-2-epimerase was identified from the genome (*DNA Research*, 3:109, 1996; *Nucleic Acids Research*, 26:63, 1998).

Meanwhile, Korean Patent Publication 10-2001-0102019 relates to N-acetylglucosamine-2-epimerase and DNA encoding the enzyme and discloses the use of DNA encoding N-acetylglucosamine-2-epimerase, which the inventors found in *Synechocystis*, a kind of *Cyanobacteria*.

Also, Korean Patent Publication 10-2006-0010706 discloses a method for producing CMP-N-acetylneuraminic acid either by adding cytidine monophosphate (CMP), N-acetylglucosamine, pyruvic acid and yeast to a recombinant strain transformed with a co-expression vector containing a gene encoding N-acetylglucosamine-2-epimerase and a gene encoding N-acetylneuraminic acid aldolase, thus producing neuraminic acid, and then adding CMP-N-acetylneuraminic acid synthetase to the produced neuraminic acid, or by adding cytidine monophosphate (CMP), N-acetylglucosamine, pyruvic acid and yeast to a recombinant strain transformed with a co-expression vector containing a gene encoding N-acetylneuraminic acid aldolase and a gene encoding CMP-N-acetylneuraminic acid synthetase. However, the method has problems in that several steps should be carried out to produce CMP-N-acetylneuraminic acid and in that cytidine monophosphate (CMP) that is used as a substrate is converted into cytidine triphosphate (CTP) in low yield.

Accordingly, the present inventors have made extensive efforts to develop a method for producing CMP-N-acetyl-neuraminic acid in an economical and simple manner. As a result, the present inventors have found a novel N-acetylglu-cosamine-2-epimerase enzyme in *Bacteroides fragilis* NCTC 9343 and confirmed that CMP-N-acetylneuraminic acid can be produced in high yield through a one-pot reaction using a mixture of various substrates and enzymes, including N-acetylglucosamine-2-epimerase, obtained by transforming the gene for said enzyme with a recombinant vector, inexpensive substrate cytidine monophosphate (CMP) and a very small amount of NTP, thereby completing the present invention.

SUMMARY OF THE INVENTION

It is a main object of the present invention to provide a novel N-acetylglucosamine-2-epimerase and a method for preparing the N-acetylglucosamine-2-epimerase, which comprises culturing recombinant microorganisms transformed with a recombinant vector containing a gene encoding said enzyme.

Another object of the present invention is to provide a method for preparing CMP-N-acetylneuraminic acid through a one-pot reaction using said N-acetylglucosamine-2-epimerase and a mixture of various substrates and enzymes.

To achieve the above objects, the present invention provides an N-acetylglucosamine-2-epimerase having an amino acid sequence of SEQ ID NO: 2.

The present invention also provides a gene encoding said N-acetylglucosamine-2-epimerase, a recombinant vector containing said gene, a recombinant microorganism transformed with said recombinant vector, and a method for preparing said N-acetylglucosamine-2-epimerase, the method comprises culturing said recombinant microorganism; and recovering said N-acetylglucosamine-2-epimerase.

The present invention also provides a method for preparing N-acetyl-D-mannosamine, the method comprises: reacting a reaction mixture containing N-acetyl-D-glucosamine in the presence of said N-acetylglucosamine-2-epimerase; and recovering said N-acetyl-D-mannosamine.

The present invention also provides a method for preparing neuraminic acid, the method comprises: reacting a reaction mixture containing pyruvic acid and N-acetyl-D-mannosamine in the presence of N-acetylneuraminic acid aldolase (NeuNAc aldolase); and recovering said neuraminic acid.

The present invention also provides a method for preparing CMP-N-acetylneuraminic acid, the method comprises: reacting a reaction mixture containing (i) cytidine 5'-monophosphate (CMP), (ii) nucleotide tri-phosphate (NTP) or ATP, (iii) acetyl phosphate (Pi), (iv) N-acetyl-D-glucosamine and (v) pyruvic acid, in the presence of (a) N-acetylglucosamine-2-epimerase (GlcNAc 2-epimerase), (b) N-acetylneuraminic acid aldolase (NeuNAc aldolase), (c) cytidine 5'-monophosphate kinase (CMP kinase), (d) acetate kinase and (e) CMP-N-acetylneuraminic acid synthetase (CMP-NeuNAc synthetase); and recovering said CMP-N-acetylneuraminic acid.

Other features and aspects of the present invention will be apparent from the following detailed description and the appended claims.

DETAILED DESCRIPTION OF THE INVENTION, AND PREFERRED EMBODIMENTS

In one aspect, the present invention relates to an N-acetyl-glucosamine-2-epimerase enzyme which is involved in the synthesis of CMP-N-acetylneuraminic acid, a gene encoding said N-acetylglucosamine-2-epimerase, a recombinant vector containing said gene, recombinant microorganisms transformed with said recombinant vector, and a method for preparing N-acetylglucosamine-2-epimerase, which comprises culturing said recombinant microorganisms.

In the present invention, said gene preferably has a base sequence of SEQ ID NO: 1. Said N-acetylglucosamine-2-epimerase is an enzyme derived from *Bacteroides fragilis* NCTC 9343 and shows a similarity of 35.06-32.9% with the corresponding genes of *Synechocystis* sp. and *Bacteroides thetaiotaomicron*.

In another aspect, the present invention relates to methods for preparing N-acetyl-D-mannosamine and neuraminic acid, characterized in that said N-acetylglucosamine-2-epimerase is used.

In still another aspect, the present invention relates to a method for preparing CMP-N-acetylneuraminic acid through a one-pot reaction using said N-acetylglucosamine-2-epimerase.

The CMP-N-acetylneuraminic acid according to the present invention can be produced by allowing a reaction mixture, containing (i) cytidine 5'-monophosphate (CMP), (ii) nucleotide tri-phosphate (NTP) or ATP, (iii) acetyl phosphate (Pi), (iv) N-acetyl-D-glucosamine and (v) pyruvic acid, to react in the presence of (a) N-acetylglucosamine-2-epimerase (GlcNAc 2-epimerase), (b) N-acetylneuraminic acid aldolase (NeuNAc aldolase), (c) cytidine 5'-monophosphate kinase (CMP kinase), (d) acetate kinase and (e) CMP-N-acetylneuraminic acid synthetase (CMP-NeuNAc synthetase).

According to the present invention, cytidine tri-phosphate (CTP) is synthesized from inexpensive substrate cytidine monophosphate (CMP) in a high yield of more than 97% via cytidine diphosphate (CDP) by CMP-kinase and acetate kinase. As a phosphate donor for said CDP, a very small amount of NTP is used, and NDP is economical in that it is reused by excess acetyl Pi and acetate kinase. Particularly, in the present invention, a complicated process for removing ADP remaining as an impurity after completion of the reaction can be eliminated through the use of CTP instead of ATP as the phosphate donor for CDP.

Figure 1:
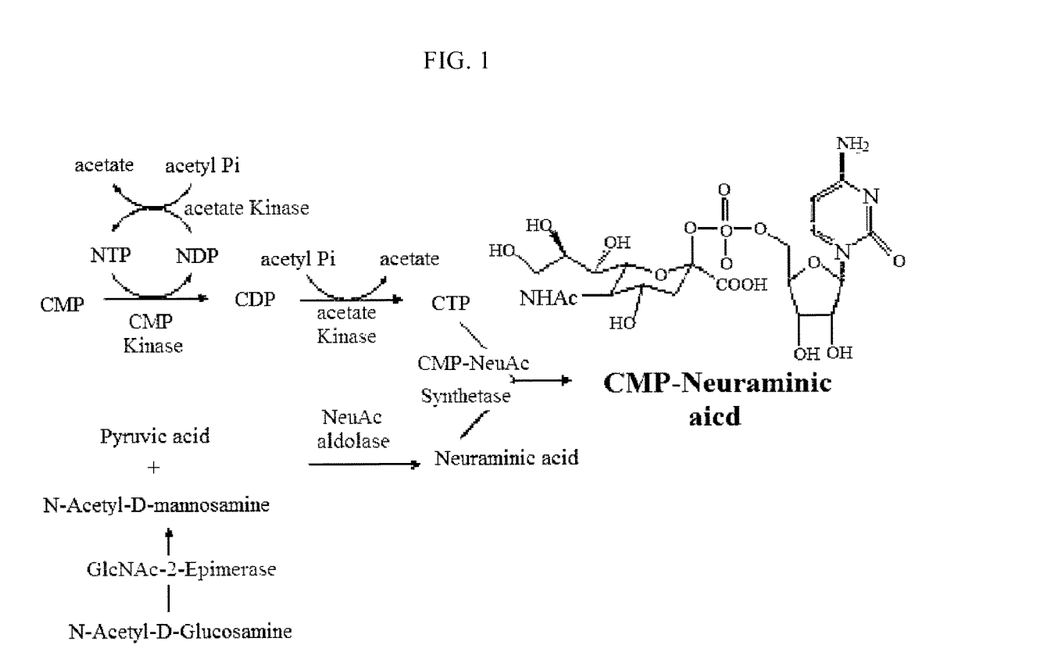
FIG. 1 is a schematic diagram showing a process for synthesizing CMP-N-acetylneuraminic acid.

Also, N-acetyl-D-glucosamine (GlacNAc) is converted into N-acetyl-D-mannosamine (ManNAc) by the N-acetylglucosamine-2-epimerase according to the present invention, and neuraminic acid is synthesized from ManNAc and pyruvic acid by NeuAc aldolase. The above-synthesized CTP and neuraminic acid are synthesized into CMP-N-acetylneuraminic acid by CMP-NeuAc synthetase (FIG. 1).

In the present invention, said nucleotide tri-phosphate (NTP) or ATP is preferably regenerated by acetyl Pi and acetate kinase, and said nucleotide tri-phosphate (NTP) is preferably cytidine tri-phosphate (CTP).

In the present invention, said N-acetylglucosamine-2-epimerase, N-acetylneuraminic acid aldolase, cytidine 5'-monophosphate kinase, acetate kinase and CMP-N-acetylneuraminic acid synthetase are preferably immobilized on a carrier, and said N-acetylglucosamine-2-epimerase, N-acetylneuraminic acid aldolase, cytidine 5'-monophosphate kinase, acetate kinase and CMP-N-acetylneuraminic acid synthetase are preferably encoded by base sequences of SEQ ID NO: 1, SEQ ID NO: 5, SEQ ID NO: 8, SEQ ID NO: 11 and SEQ ID NO: 14, respectively.

According to the present invention, the synthesis cost of the CMP-N-acetylneuraminic acid can be greatly reduced, because the CMP-N-acetylneuraminic acid can be synthesized in a one-step process by purifying each of highly expressed enzymes and immobilizing the purified enzymes on polymer beads such as chitosan, without carrying out repeated synthesis steps. The immobilization of the enzymes can be performed using conventional enzyme immobilization means (covalent adhesion, crosslinking using a multifunctional reagent, adsorption, microencapsulation, etc.). The purification of the enzymes can be performed using conventional enzyme purification means (salting out, isoelectric precipitation, dialysis, various chromatography processes, etc.), coenzymes or purified enzymes, obtained using said purification process, can be used, and the process of immobilizing said enzymes on polymer beads can be performed using a conventional enzyme immobilization process. The enzymes purified using said process can be used more than 20 times in a state in which they are immobilized on polymer beads, and thus the cost and procedures for recovering the enzymes can be reduced.

According to the present invention, a mixture of said various substrates and enzymes are subjected to a one-pot reaction, and thus, the reactivity of each enzyme can be maximized, and CMP-N-acetylneuraminic acid can be synthesized in a high yield of more than 90%, even if small amounts of enzymes and substrates are used. Specifically, in the case where N-acetylglucosamine-2-epimerase reacts alone, the synthesis yield of CMP-N-acetylneuraminic acid will be less than 50%, but when the one-pot reaction is carried out, CMP-N-acetylneuraminic acid can be synthesized in a high yield of more than 90%.

N-acetylneuraminic acid aldolase, CMP-kinase, acetate kinase and CMP-N-acetylneuraminic acid synthetase, which are used in the present invention, are known enzymes and can be prepared according to the conventional methods. However, it is preferable to prepare the enzymes using recombinant DNA techniques, including the cloning of said genes, the construction of recombinant vectors containing the cloned DNA fragments, the construction of transformants containing the recombinant vectors introduced therein, and the production of target enzyme proteins through the culture of the transformants. A host cell for use in transformation is not specifically limited, but it is preferable to use *E. coli* in view of manipulation and convenience.

As N-acetylglucosamine-2-epimerase used in the present invention, a novel N-acetylglucosamine-2-epimerase-encoding gene, isolated from *Bacteroides fragilis* NCTC 9343, was used. The entire sequence of the genomic DNA of *Bacteroides fragilis* was determined (U.S. Pat. No. 7,090,973), but the function of the N-acetylglucosamine-2-epimerase gene is not yet known.

As used herein, the term "vector" refers to a DNA construct containing a DNA sequence which is operably linked to a suitable control sequence capable of effecting the expression of the DNA in a suitable host. The examples of the vector include plasmids, phage particles, or simply potential genomic inserts. Once transformed into a suitable host, the vector may replicate and function independently of the host genome, or may, in some instances, integrate into the genome itself. As used herein, the term "plasmid" and "vector" are sometimes used interchangeably, because the plasmid is the most commonly used form of vector at present. For the purpose of the present invention, the plasmid vector is preferably used. A typical plasmid vector which can be used for this purpose contains the following: (a) a replication origin by which replication occurs efficiently such that several hundred plasmid vectors per host cell are created; (b) an antibiotic-resistant gene by which host cells transformed with the plasmid vector can be selected; and (c) restriction enzyme digestion sites into which foreign DNA fragments can be inserted. Even if suitable restriction enzyme digestion sites are not present in the vector, the use of a conventional synthetic oligonucleotide adaptor or linker enables the easy ligation between the vector and the foreign DNA fragments.

After ligation, the vector should be transformed into suitable host cells. The transformation can be easily achieved using the well-known calcium chloride method. Selectively electroporation (Neumann et al., *EMBO J.*, 1:841, 1982) can also be used in the transformation of such host cells.

For the overexpression of a gene, an expression vector known in the art may be used in the present invention.

A nucleic acid is "operably linked" when it is placed into a functional relationship with another nucleic acid sequence. By "operably linked" is meant that a gene and a regulatory sequence(s) are connected in such a way as to permit gene expression when the appropriate molecules (e.g., transcriptional activator proteins) are bound to the regulatory sequence(s). For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and present in open reading frame. However, enhancers do not have to be contiguous. Linking is accomplished by ligation at convenient restriction sites. If such sites do not exist, the synthetic oligonucleotide adaptors or linkers are used in accordance with conventional practice.

As well-known to the art, in order to increase expression level of a transfected gene in a host cell, the gene should be operably linked to transcriptional and translational control sequences which can work in a selected expression host. Preferably, the corresponding gene and expression control sequence are contained in an expression vector comprising a selection marker and replication origin. When an expression host is a eukaryotic cell, the expression vector should further comprise an expression marker useful in the eukaryotic expression host cell.

The host cell transformed with said recombinant vector constitutes another aspect of the present invention. As used herein, the term "transformation" refers to introducing DNA into a host cell so that the DNA is replicable, either as a chromosomal integrant or as an extrachromosomal element.

Of course, it should be understood that all the vectors do not function equally to express the DNA sequences according to the present invention. Likewise, all the host cells do not function equally for the same expression system. However, those skilled in the art may properly select a vector, expression control sequence and host cell without departing from the scope of the present invention and without undue experimentation. For example, in selection of a vector, a host cell must be considered. This is because the vector should be replicated therein. Also, the replication number and ability to control the replication number of a vector and expression of other proteins encoded by the vector, for example, antibiotic marker, should be considered.

EXAMPLES

Hereinafter, the present invention will be described in further detail with reference to examples. It will be apparent to one skilled in the art that these examples are for illustrative purpose only and are not construed to limit the scope of the present invention.

Example 1

Cloning and Transformation of Genes 1-1: Cloning and Transformation of nanE Gene (SEQ ID NO: 1) Encoding N-Acetylglucosamine-2-Epimerase In order to eliminate the step of isomerizing N-acetyl-D-glucosamine into N-acetyl-D-mannosamine, which was pointed out as the biggest problem in achieving the goal of increasing the preparation yield of CMP-N-acetylneuraminic acid and reducing the production cost, N-acetylglucosamine-2-epimerase (GlcNAc 2-epimerase) was sought from various sources.

Three kinds of N-acetylglucosamine-2-epimerase-like genes were found from anaerobic microorganism *Bacteroides fragilis* NCTC 9343 (NC_003228).

The candidate gene No. 1 for N-acetylglucosamine-2-epimerase was in the region of 947856-949034, had a size of 1179 bp, and showed a similarity of 23.68-24.44% with the corresponding genes of *Rhizobium meliloti* and *Homo sapiens*.

The candidate gene No. 2 for N-acetylglucosamine-2-epimerase was in the range of 1996625-1997809, had a size of 1185 bp and showed a similarity of 35.06-32.9% with the corresponding genes of *Synechocystis* sp. and *Bacteroides thetaiotaomicron*.

The candidate gene No. 3 for N-acetylglucosamine-2-epimerase was in the range of 4765592-4766353, had a size of 762 bp and showed a similarity of 48.18-34.97% with the corresponding genes of *Rhodopirellula baltica* and *Synechocystis* sp.

Each of the genes was inserted into a pET expression vector (Novagen), which was then transformed into BL21 (DE3) pLysS expression strain. As a result, it was observed that the candidate gene Nos. 1 and 2 for N-acetylglucosamine-2-epimerase were highly expressed as soluble proteins, but the candidate gene No. 3 was not expressed as a soluble protein, but was expressed as an insoluble protein.

In order to examine the activities of the highly expressed candidate gene Nos. 1 and 2, the candidate gene Nos. 1 and 2 for N-acetylglucosamine-2-epimerase and N-acetylneuraminic acid aldolase, the activity of which was determined, were allowed to react in a one-step process using N-acetyl-D-glucosamine and pyruvic acid as substrates. The produced neuraminic acid was analyzed using a sugar analysis system (Metrohm).

As a result, it could be seen that the candidate gene No. 1 for N-acetylglucosamine-2-epimerase had no activity, and the gene No. 2 for N-acetylglucosamine-2-epimerase candidate had excellent activity. Also, the activities of the candidate genes were compared with the activity of human N-acetylglucosamine-2-epimerase (organism="Homo sapiens, ene="RENBP", coded_by="NM_002910.4:203..1456") under the same conditions (50 mM N-acetyl D-glucosamine, 100-200 mM pyruvic acid, 10 mM $MgCl_2$, 50 mM-100 mM Tris HCl, 30-40° C.) and, as a result, the gene No. 2 for N-acetylglucosamine-2-epimerase candidate showed a very high reaction rate and yield. Accordingly, the candidate gene No. 2 was selected as N-acetylglucosamine-2-epimerase.

In order to clone the nanE gene (SEQ ID NO: 2) encoding N-acetylglucosamine-2-epimerase (GlcNAc 2-epimerase), the nanE gene was amplified by PCR using the chromosomal DNA of the *Bacteroides fragilis* NCTC 9343 as a template and primers of SEQ ID NO: 3 and SEQ ID NO: 4.

```
SEQ ID NO: 3:
5'-ct gcc atg gtt atg aat act aca g

SEQ ID NO: 4:
5'-aat gga tcc tta ttt ttc tga cag
```

The PCR amplification was performed using a mixture of 1 μl (10 pmol) of DNA, 1 μl of each of primers, 4 μl of Primix (Genotech) and 14 μl of distilled water in the Mastercycler gradient PCR system (Ependorf) for 30 cycles of denaturation at 96° C. for 1 min, annealing at 40.2° C. for 1 min and elongation at 72° C. for 2 min.

Figure 2:
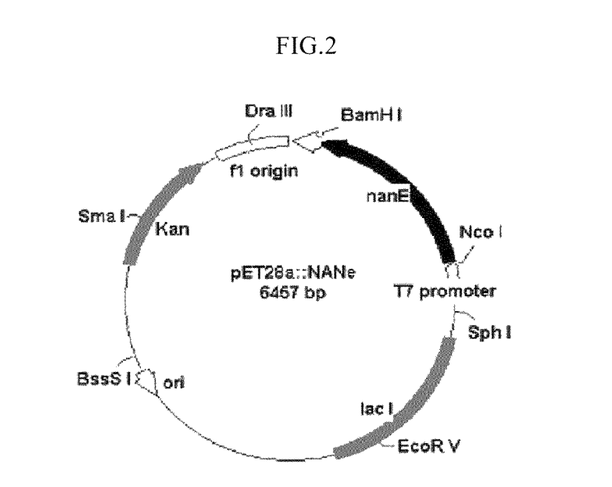
FIG. 2 shows a recombinant vector containing an N-acetyl-glucosamine-2-epimerase-encoding gene (nanE).

The amplified PCR product was purified with a plasmid mini-prep kit (Solgent), and the DNA was precipitated by the addition of 70% ethanol. The precipitated DNA was analyzed by agarose gel electrophoresis to purify a 1.2-kb DNA fragment. The purified DNA was digested with restriction enzymes NcoI and BamHI and ligated to plasmid pET28a(+) (Novagen) T4 DNA (Takara), digested with the same restriction enzymes NcoI and BamHI, using ligase (FIG. 2).

The recombinant vector was introduced into *E. coli* XL-Blue to obtain kanamycin-resistant transformants, thus isolating plasmid pNANEe therefrom. The pNANEe plasmid was a plasmid in which the DNA fragment containing a structural gene of the nanE gene of *Bacteroides fragilis* was inserted into the NcoI-BamHI digestion sites downstream of the T7 promoter of pET28a(+).

The recombinant gene was introduced into high-expression strain *E. coli* BL21(DE3) (Invitrogen) using a method for introducing the plasmid into the strain by treatment with calcium chloride (*J. Mol. Biol.*, 53:159, 1970). The resulting transformant was named "*E. coli*/pNANe".

1-2: Cloning and Transformation of nanA Gene Encoding N-Acetylneuraminic Acid Aldolase In order to clone the nanA gene (SEQ ID NO: 5) encoding N-acetylneuraminic acid aldolase NeuNAc aldolase, the nanA gene was amplified by PCR using the chromosomal DNA of an *E. coli* K-12 C600 as a template and primers of SEQ ID NO: 6 and SEQ ID NO: 7.

```
SEQ ID NO: 6:
5'-ggtatccatggcaacgaatttacg

SEQ ID NO: 7:
5'-ggtaggctcgagcgaggggaaac
```

The PCR amplification was performed using a mixture of 1 μl (10 pmol) of DNA, 1 μl of each of primers, 4 μl of Primix (Genotech) and 14 μl of distilled water in the Mastercycler gradient PCR system (Ependorf) for 30 cycles of denaturation at 96° C. for 1 min, annealing at 50.2° C. for 1 min and elongation at 72° C. for 2 min.

Figure 3:
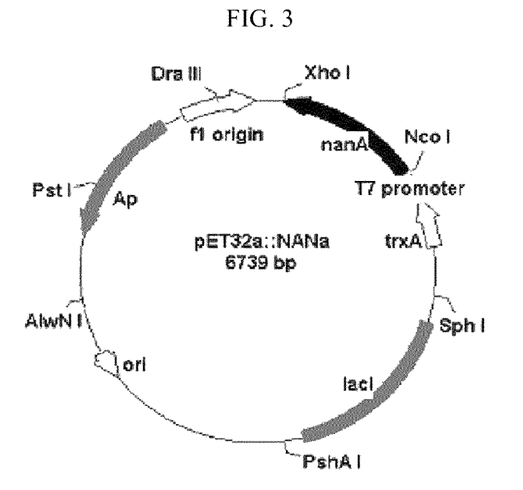
FIG. 3 shows a recombinant vector containing an N-acetyl-neuraminic acid aldolase-encoding gene (nan).

The amplified PCR product was purified with a plasmid mini-prep kit (Solgent), and the DNA was precipitated by the addition of 70% ethanol. The precipitated DNA was analyzed by agarose gel electrophoresis to purify a 0.9-kb DNA fragment. The purified DNA was digested with restriction enzymes NcoI and XhoI and ligated to plasmid pET32a(+) (Novagen) T4 DNA (Takara), digested with the same restriction enzymes NcoI and XhoI, using ligase (FIG. 3). The resulting vector was transformed into *E. coli* XL-Blue to obtain ampicillin-resistant transformants, thus isolating plasmid pNANa therefrom. The plasmid pNANa was a plasmid in which the DNA fragment containing a structural gene of the nanA gene of *E. coli* K-12 C600 was inserted into the NcoI-XhoI digestion sites downstream of the T7 promoter of pET32a(+).

The recombinant gene was introduced into high-expression strain *E. coli* BL21(DE3)pLysS (Invitrogen) using a method for introducing the plasmid into the strain by treatment with calcium chloride (*J. Mol. Biol.*, 53:159, 1970). The resulting transformant was named "*E. coli*/pNANa".

1-3: Cloning and Transformation of Cmk Gene Encoding Cytidine 5'-Monophosphate Kinase In order to clone the cmk gene (SEQ ID NO: 8) encoding cytidine 5'-monophosphate kinase, the cmk gene was amplified by PCR using the chromosomal DNA of an *E. coli* K-12 as a template and primers of SEQ ID NO: 9 and SEQ ID NO: 10.

```
SEQ ID NO: 9:
5'-cat atg acggca att gcc ccg gtt att ac

SEQ ID NO: 10:
5'-gaa ttc ggt cgc tta tgc gag agc c
```

The PCR amplification was performed using a mixture of 1 μl (10 pmol) of DNA, 1 μl of each of primers, 4 μl of Primix (Genotech) and 14 μl of distilled water in the Mastercycler gradient PCR system (Ependorf) for 30 cycles of denaturation at 96° C. for 1 min, annealing at 55.7° C. for 1 min and elongation at 72° C. for 2 min.

Figure 4:
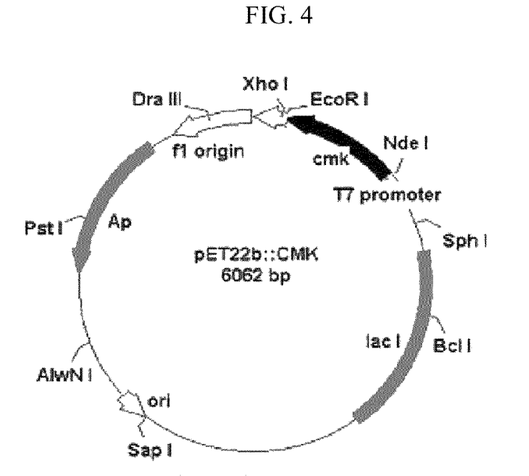
FIG. 4 shows a recombinant vector containing a 5'-monophosphate kinase-encoding gene (cmk).

The amplified PCR product was purified with a plasmid mini-prep kit (Solgent), and the DNA was precipitated by the addition of 70% ethanol. The precipitated DNA was analyzed by agarose gel electrophoresis to purify a 0.7-kb DNA fragment. The purified DNA was digested with restriction enzymes NdeI and EcoRI and ligated to plasmid pET22b(+) (Novagen) T4 DNA(Takara), digested with the same restriction enzymes NdeI and EcoRI, using ligase (FIG. 4). The resulting vector was introduced into *E. coli* XL-Blue to obtain ampicillin-resistant transformants, thus isolating plasmid pCMK therefrom. The plasmid pCMK was a plasmid in which the DNA fragment containing a structural gene of the cmk gene of *E. coli* K-12 C600 was inserted into the NdeI and EcoRI digestion sites downstream of the T7 promoter of pET22b(+).

The recombinant gene was introduced into high-expression strain *E. coli* BL21(DE3)pLysS (Invitrogen) using a method for introducing the plasmid into the strain by treatment with calcium chloride (*J. Mol. Biol.*, 53:159, 1970). The resulting transformant was named "*E. coli*/pCMK".

1-4: Cloning and Transformation of ack Gene Encoding Acetate Kinase

In order to clone the ack gene (SEQ ID NO: 11) encoding acetate kinase, the ack gene was amplified by PCR using the chromosomal DNA of an *E. coli* K-12 as a template and primers of SEQ ID NO: 12 and SEQ ID NO: 13.

```
SEQ ID NO: 12:
5'-catatgtcgagtaagttagtttctg

SEQ ID NO: 13:
5'-gaatcctcaggcagtcaggcggctcgcgtc
```

The PCR amplification was performed using a mixture of 1 μl (10 pmol) of DNA, 1 μl of each of primers, 4 μl of Primix (Genotech) and 14 μl of distilled water in the Mastercycler gradient PCR system (Ependorf) for 30 cycles of denaturation at 96° C. for 1 min, annealing at 58.7° C. for 1 min and elongation at 72° C. for 2 min.

Figure 5:
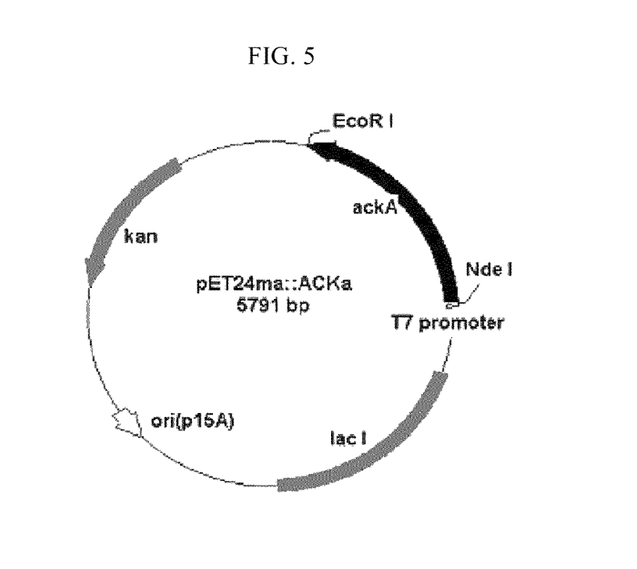
FIG. 5 shows a recombinant vector containing an acetate kinase-encoding gene (ack).

The amplified PCR product was purified with a plasmid mini-prep kit (Solgent), and the DNA was precipitated by the addition of 70% ethanol. The precipitated DNA was analyzed by agarose gel electrophoresis to purify a 1.2-kb DNA fragment. The purified DNA was digested with restriction enzymes NdeI and EcoRI and ligated to plasmid pET24ma (+)(Novagen) T4 DNA(Takara), digested with the same restriction enzymes NdeI and EcoRI, using ligase (FIG. 5). The resulting vector was introduced into *E. coli* XL-Blue to obtain kanamycin-resistant transformants, thus isolating plasmid pACKa therefrom.

The plasmid was a plasmid in which the DNA fragment containing a structural gene of the ackA gene of *E. coli* K-12 C600 was inserted into the NdeI and EcoRI digestion sites downstream of the T7 promoter of pET24ma(+).

The recombinant gene was introduced into high-expression strain *E. coli* BL21(DE3)pLysS (Invitrogen) using a method for introducing the plasmid into the strain by treatment with calcium chloride (*J. Mol. Biol.*, 53:159, 1970). The resulting transformant was named "*E. coli*/pACKa".

1-5: Cloning and Transformation of neu Gene Encoding CMP-N-Acetylneuraminic Acid Synthetase In order to clone the neu gene (SEQ ID NO: 14) encoding CMP-NeuNAc synthetase, the neu gene was amplified by PCR using the chromosomal DNA of a *Neisseria meningitides* (Koram Biotech) as a template and primers of SEQ ID NO: 15 and SEQ ID NO: 16.

SEQ ID NO: 15:
5'-aagcatatggaaaaacaaaatattgcg

SEQ ID NO: 16:
5'-gtggaattcttagctttccttgtg

The PCR amplification was performed using a mixture of 1 μl (10 pmol) of DNA, 1 μl of each of primers, 4 μl of Primix (Genotech) and 14 μl of distilled water in the Mastercycler gradient PCR system (Ependorf) for 30 cycles of denaturation at 96° C. for 1 min, annealing at 57.7° C. for 1 min and elongation at 72° C. for 2 min.

Figure 6:
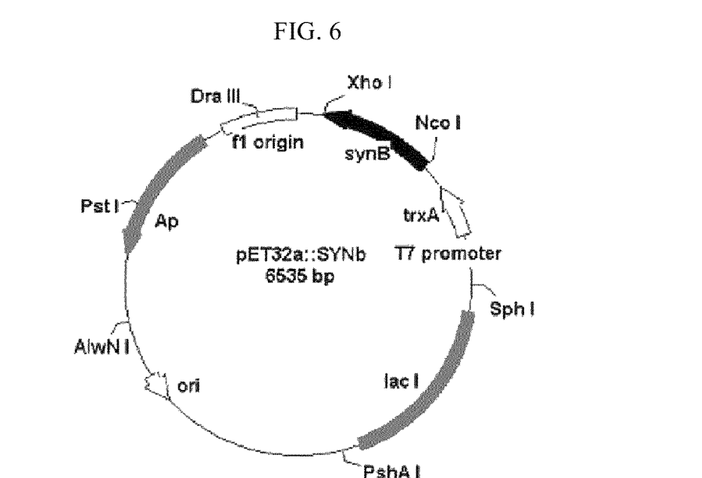
FIG. 6 shows a recombinant vector containing a CMP-N-acetylneuraminic acid synthetase-encoding gene (neu).

The amplified PCR product was purified with a plasmid mini-prep kit (Solgent), and the DNA was precipitated by the addition of 70% ethanol. The precipitated DNA was analyzed by agarose gel electrophoresis to purify a 0.7-kb DNA fragment. The purified DNA was digested with restriction enzymes NdeI and EcoRI and ligated to plasmid pET32a(+) (Novagen) T4 DNA (Takara), digested with the same restriction enzymes NdeI and EcoRI, using ligase (FIG. 6). The resulting vector was introduced into E. coli XL-Blue to obtain ampicillin-resistant transformants, thus isolating plasmid pSYNb therefrom. The plasmid pSYNb was a plasmid in which the DNA fragment containing a structural gene of the synB gene of Neisseria meningitidis was inserted into the NdeI and EcoRI digestion sites downstream of the T7 promoter of pET24ma(+).

The recombinant gene was introduced into high-expression strain E. coli BL21(DE3) (Invitrogen) using a method for introducing the plasmid into the strain by treatment with calcium chloride (J. Mol. Biol., 53:159, 1970). The resulting transformant was named "E. coli/pSYNb".

Example 2

Analysis of Enzyme Expression 500 ml of seed culture, obtained by culturing each of the transformants E. coli/pNANe, E. coli/pNANa, E. coli/pCMK, E. coli/pACKa and E. coli/pSYNb in LB medium, was inoculated into 5 liters of LB medium. When the cell density ($OD_{600}$) reached about 3-5, the cells were harvested. The culture conditions of the transformants containing the respective enzymes are shown in Table 1 below.

Figure 7:
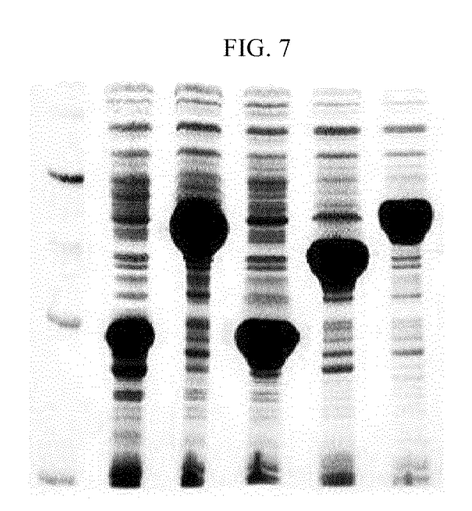
FIG. 7 shows the results of SDS-PAGE gel analysis conducted to examine whether each of enzymes was expressed (lane 1: marker; lane 2: cytidine 5'-monophosphate kinase; lane 3: acetate kinase; lane 4: CMP-N-acetylneuraminic acid synthetase; lane 5: N-acetylneuraminic acid aldolase; and lane 6: acylglucosamine-2-epimerase).

The harvested cells were disrupted with an ultrasonic disruptor or a French press, and then the expression of each of the enzymes was analyzed by SDS-PAGE gel (FIG. 7).

As a result, it could be observed that the enzyme encoded by the gene inserted into each of the transformants was overexpressed.

TABLE 1

Culture conditions of strain preparing each of enzymes

| Enzymes | Seed culture condition | Main culture condition | IPTG conc. (5 L culture) | Expression inducing condition |
|---|---|---|---|---|
| cytidine 5'-monophosphate kinase (CMK) | 37° C. (ampicillin) | 37° C., pH 7.0 | 1M IPTG 5 ml | 37° C., 12 h ($OD_{600}$ = 3~5) |
| acetate kinase (ACK) | 37° C. (kanamycin) | 37° C., pH 7.0 | 1M IPTG 5 ml | 37° C., 12 h ($OD_{600}$ = 3~5) |
| CMP-N-acetylneuraminic acid synthetase (NEU) | 37° C. (ampicillin)) | 37° C., pH 7.0 | 1M IPTG 2 ml | 20° C., 12 h ($OD_{600}$ = 3~5) |

TABLE 1-continued

Culture conditions of strain preparing each of enzymes

| Enzymes | Seed culture condition | Main culture condition | IPTG conc. (5 L culture) | Expression inducing condition |
|---|---|---|---|---|
| N-acetylneuraminic acid aldolase (NAN) | 37° C. (ampicillin) | 37° C., pH 7.0 | 1M IPTG 5 ml | 37° C., 12 h ($OD_{600}$ = 3~5) |
| N-acetylglucosamine-2-epimerase | 37° C. (kanamycin) | 37° C., pH 7.0 | 1M IPTG 5 ml | 37° C., 12 h ($OD_{600}$ = 3~5) |

Example 3

Purification of Enzymes

Said N-acetylglucosamine-2-epimerase (GlcAc 2-epimerase), N-acetylneuraminic acid aldolase (NeuAc aldolase), cytidine 5'-monophosphate kinase, acetate kinase and CMP-N-acetylneuraminic acid synthetase (CMP-NeuAc synthetase) were precipitated with ammonium sulfate and purified with an ion exchange resin column (Protein purification techniques, $2^{nd}$ edition, Oxford University Press, 2001).

The concentration of ammonium sulfate used for the precipitation of each of the enzymes can be adjusted appropriately as in the range of 30-80%. Each of the enzymes was precipitated with ammonium sulfate in a refrigerator at less than 10° C., and preferably 3-5° C., with stirring for 1-5 hours.

Figure 8:
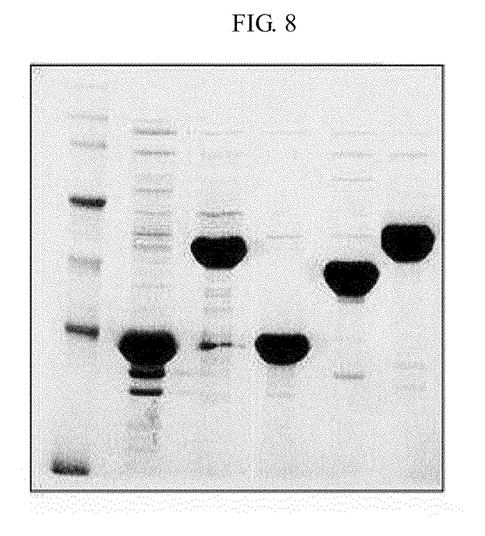
FIG. 8 shows the results of SDS-PAGE gel analysis conducted to examine whether each of purified enzymes was expressed (lane 1: marker; lane 2: purified cytidine 5'-monophosphate kinase; lane 3: purified acetate kinase; lane 4: purified CMP-N-acetylneuraminic acid synthetase; lane 5: purified N-acetylneuraminic acid aldolase; and lane 6: purified acylglucosamine-2-epimerase).

The precipitated enzymes were dissolved in a minimal amount of 50 mM Tris HCl (pH7.5) buffer and desalted through a dialytic membrane. The purified and concentrated enzyme solutions were purified on a UNO sphere Q (Bio-RAD) column packed with strong ion exchange resin, using a gradient elusion with eluent A (20 mM Tris HCl (pH7.5)) and eluent B (20 mM Tris HCl/1M NaCl (pH7.5)) as eluents. The purified enzymes were analyzed by SDS-PAGE gel (FIG. 8).

Example 4

Immobilization of Enzymes 3 liters of 2.5% glutaraldehyde was added to 1 kg (about 1 liter) of polymer beads, and then stirred at room temperature for 2 hours to activate the polymer beads. The activated polymer beads were filtered and then washed, and each of the enzymes purified in Example 3 was added to the polymer beads in an amount of 3 mg per g of the polymer beads. Then, the mixture was stirred at room temperature for 6 hours to immobilize the enzymes on the polymer beads. The degree and quantification of the immobilization of the enzymes were analyzed using the Bradford method (Anal. Biochem., 72:248, 1976).

Example 5

Synthesis of CMP-N-Acetylneuraminic Acid

A reaction mixture of 20-100 g of 20-80 mM cytidine 5'-monophosphate (CMP, Shanghai QZU Bioscience & Biotechnology), 34.15-136.6 g of 20-80 mM N-acetyl-D-glucosamine (Shanghai Jiubang Chemical), 33.9-101.7 g of 40-120 mM pyruvic acid, 30.9 g of 20 mM $MgCl_2.H_2O$ (Duksan), 3.72 g of 1 mM CTP (Sigma), 84-525 g of 80-500 mM acetyl phosphate (Sigma) and 7 liters of 50 mM Tris HCl buffer (pH 7.0), maintained at pH 6.5-8.0 using 2M NaOH at 37° C., was mixed with the polymer beads prepared in Example 4, which have each of cytidine monophosphate kinase (CMK), acetate kinase (ACK), NeuAc aldolase (NAN), CMP-NeuAc synthetase (NEU) and GlcNAc-2-epimerase immobilized thereon. Then, the mixture was stirred in a reactor for 5-12 hours.

To separate and detect the reaction supernatant, the Thermo 42 column (Thermo Electron Corporation) was used, and the supernatant was subjected to HPLC using eluent A (100 mM $KH_2PO_4/K_2HPO_4$) and eluent B (methanol) at a ratio of 90% (eluent A):10% (eluent B). As a result, it could be seen that CMP-N-acetylneuraminic acid was synthesized in a yield of about 90%.

Example 6

Purification of CMP-Neuraminic Acid

Figure 9:
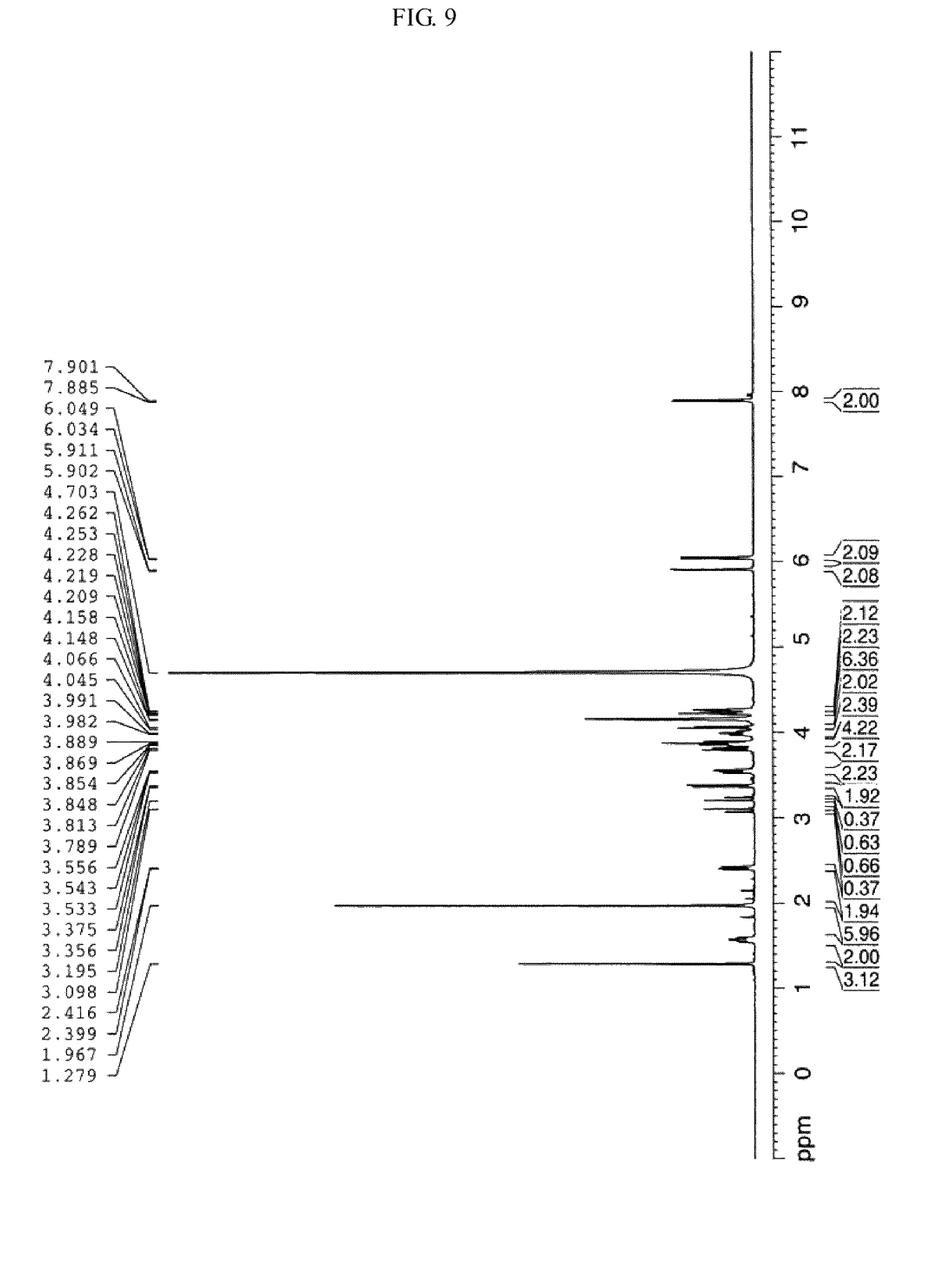
FIG. 9 shows the $^1$H NMR analysis result of CMP-N-acetylneuraminic acid.
Figure 10:
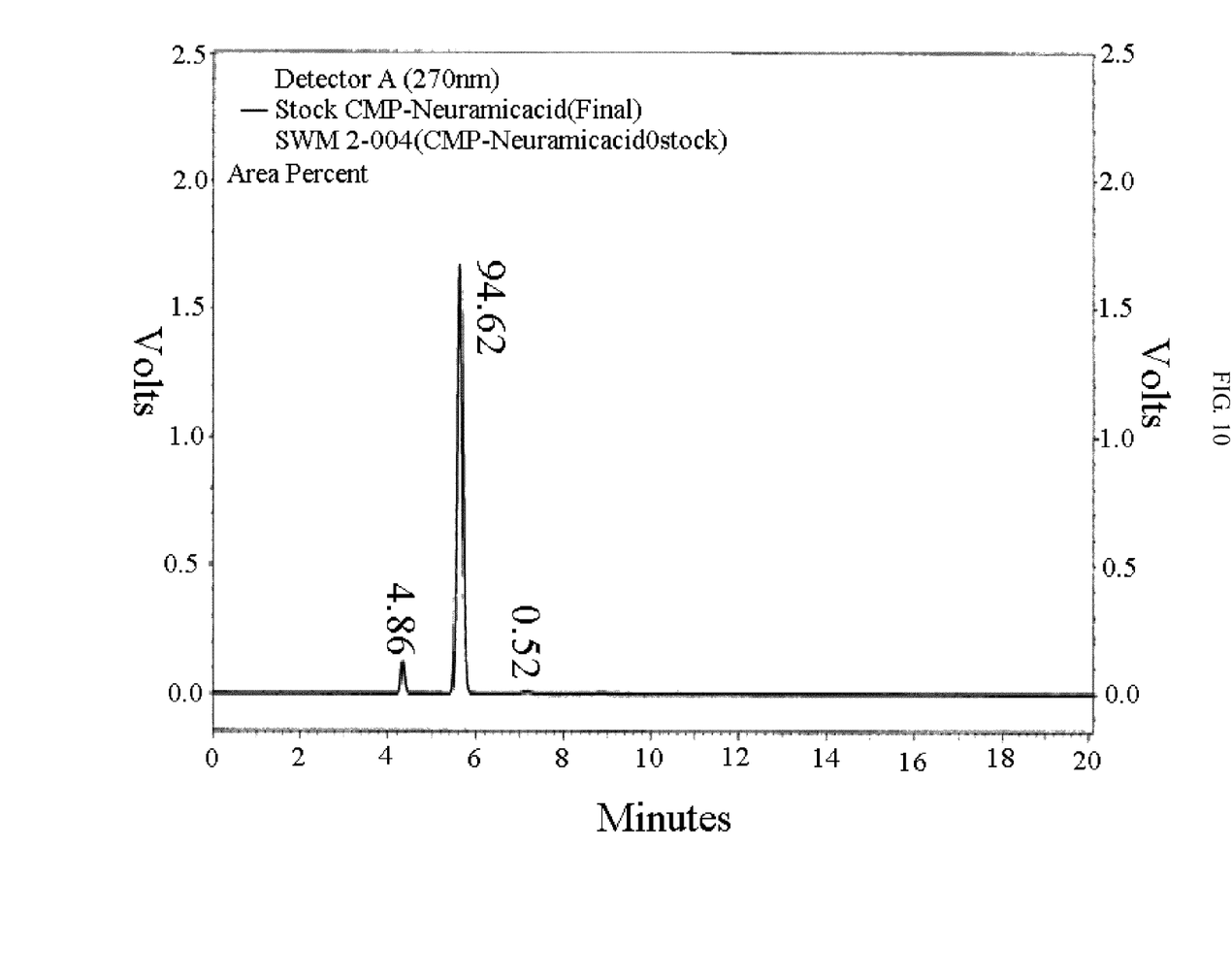
FIG. 10 shows the HPLC analysis result of CMP-N-acetyl-neuraminic acid.

The CMP-N-acetylneuraminic acid, synthesized in Example 5, was poured into the upper portion of an anion exchange resin column (Dowex-1x2; Cl⁻-form) and eluted by the salt concentration gradient. The eluent fractions the desired material were concentrated again and desalted by Sephadex G-10 gel permeation, thus obtaining a high-purity final product. The product was concentrated by freeze drying. CMP-N-acetylneuraminic acid was finally obtained in a yield of 81% through each purification step and analyzed by NMR and HPLC (FIG. 9 and FIG. 10).

INDUSTRIAL APPLICABILITY

As described in detail above, the present invention has an effect to provide a method for mass-producing CMP-N-acetylneuraminic acid using novel N-acetylglucosamine-2-epimerase. According to the present invention, CMP-N-acetylneuraminic acid can be produced in a large amount through a one-step reaction using cytidine monophosphate and N-acetyl-D-glucosamine which are inexpensive substrates. Also, CMP-N-acetylneuraminic acid can be produced at low cost, because nucleotide tri-phosphate (NTP) or ATP is regenerated by acetyl Pi and acetate kinase.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. An in vitro method for preparing a CMP-N-acetylneuraminic acid from N-acetyl-D-glucosamine, the method comprising:
reacting a reaction mixture containing (i) cytidine 5'-monophosphate (CMP), (ii) nucleotide triphosphate (NTP) or ATP, (iii) acetyl phosphate (Pi), (iv) N-acetyl-D-glucosamine and (v) pyruvic acid, in the presence of (a) N-acetylglucosamine-2-epimerase (GlcNAc 2-epimerase), (b) N-acetylneuraminic acid aldolase (NeuNAc aldolase), (c) cytidine 5'-monophosphate kinase (CMP kinase), (d) acetate kinase and (e) CMP-N-acetylneuraminic acid synthetase (CMP-NeuNAc synthetase); and recovering said CMP-N-acetylneuraminic acid.

2. The method for preparing CMP-N-acetylneuraminic acid according to claim 1, wherein said nucleotide tri-phosphate (NTP) or ATP is regenerated by acetyl Pi and acetate kinase.

3. The method for preparing CMP-N-acetylneuraminic acid according to claim 1, wherein said nucleotide tri-phosphate (NTP) is cytidine tri-phosphate (CTP).

4. The method for preparing CMP-N-acetylneuraminic acid according to claim 1, wherein said N-acetylglucosamine-2-epimerase has the amino acid sequence of SEQ ID NO: 2.

5. The method for preparing CMP-N-acetylneuraminic acid according to claim 1, wherein said N-acetylglucosamine-2-epimerase, N-acetylneuraminic acid aldolase, cytidine 5'-monophosphate kinase, acetate kinase and CMP-N-acetylneuraminic acid synthetase are immobilized on a carrier.

6. The method for preparing CMP-N-acetylneuraminic acid according to claim 1, wherein said N-acetylglucosamine-2-epimerase is encoded by polynucleotide sequence of SEQ ID NO: 1, N-acetylneuraminic acid aldolase is encoded by polynucleotide sequence of SEQ ID NO: 5, cytidine 5'-monophosphate kinase is encoded by polynucleotide sequence of SEQ ID NO: 8, acetate kinase is encoded by polynucleotide sequence of SEQ ID NO: 11, and CMP-N-acetylneuraminic acid synthetase is encoded by SEQ ID NO: 14.

* * * * *